United States Patent [19]

Tanaka

[11] 4,367,730

[45] Jan. 11, 1983

[54] WATER PROOF COVER FOR ENDOSCOPE

[75] Inventor: Hitoshi Tanaka, Iwatsuki, Japan

[73] Assignee: Fuji Photo Optical Co., Ltd., Japan

[21] Appl. No.: 202,116

[22] Filed: Oct. 30, 1980

[30] Foreign Application Priority Data

Oct. 31, 1979 [JP] Japan .................. 54-150091[U]

[51] Int. Cl.³ .............................................. A61B 1/06
[52] U.S. Cl. ........................................................ 128/6
[58] Field of Search ................................... 128/3–8; 350/57, 65; 356/241

[56] References Cited

U.S. PATENT DOCUMENTS

| 1,438,013 | 12/1922 | Benson | 350/65 |
| 2,794,360 | 6/1957 | Eagle | 350/65 |
| 2,908,198 | 10/1959 | Staudt | 350/65 |
| 3,131,477 | 5/1964 | Thomas | 350/65 |
| 3,510,196 | 5/1970 | Beer et al. | 350/65 |
| 4,240,411 | 12/1980 | Hosono | 128/4 |

Primary Examiner—Kyle L. Howell
Assistant Examiner—Max F. Hindenburg
Attorney, Agent, or Firm—Eyre, Mann, Lucas & Just

[57] ABSTRACT

An endoscope is provided with a water proof cover on its eyepiece portion or its connector portion to be connected with a light source system. The water proof cover is provided with a smooth engaging face on the internal periphery near its open end to be liquid tightly engaged with a packing ring mounted on the endoscope. There is provided a protective cover above the packing ring to prevent the ring from being damaged while the cover is removed from the endoscope. In a preferred embodiment, the water proof cover is provided with a protective sleeve which is slid into the protecting position to cover and protect the smooth engaging face while the water proof cover is removed from the endoscope. In a further preferred embodiment, the water proof cover is made into such a form as to enable the diopter ring to be rotated with the cover mounted on the endoscope.

9 Claims, 4 Drawing Figures

WATER PROOF COVER FOR ENDOSCOPE

BACKGROUND OF THE INVENTION

1. Field of the Invention

This invention relates to a water proof cover for an endoscope, and more particularly to an improvement in a water proof cover for non-water proof structure of the eyepiece portion or a connector portion of an endoscope or the like.

2. Description of the Prior Art

The endoscope for medical use is inserted into body cavities for observation, inspection and diagnosis or medical treatment. Therefore, the endoscope must always be disinfected after use. There are known two methods of disinfection. One is gas disinfection and the other is liquid disinfection. The former method of disinfection using gas needs a long period of time, and accordingly is disadvantageous in that it is impossible to use one endoscope repeatedly in a day. In view of the actual situation where it is highly desired to use the same endoscope many times in a day, the gas disinfection method is practically useless. On the other hand, the latter method of disinfection using liquid is practically advantageous in that the disinfection can be conducted in a short time and accordingly it is possible to disinfect the same endoscope many times a day thereby. However, the liquid disinfection method has a defect in that the liquid forces into the interior of the eyepiece or the connector of the endoscope of non-water proof structure. This will, of course, shorten the duration period of the endoscope and further cause a trouble or breakdown thereof. Therefore, there is a great demand for water proof of the endoscope.

SUMMARY OF THE INVENTION

The primary object of the present invention is to provide a water proof cover for an endoscope.

A more specific object of the present invention is to provide an improved water proof cover for an endoscope which can easily be manufactured at a low cost.

Another object of the present invention is to provide an improved water proof cover for an endoscope which has high performance of water proof.

A further object of the present invention is to provide a water proof cover for the eye piece of an endoscope which enables the operator of the endoscope to handle the endoscope with the cover mounted thereon.

A still another object of the present invention is to provide an improved water proof cover for an endoscope which has a protective portion to protect the smooth surface to be engaged with the water proofing packing for maintaining the high performance of water proof.

A still further object of the present invention is to provide an improved water proof cover for the eyepiece of an endoscope which enables operation of a diopter ring with the cover attached to the eyepiece.

The water proof cover for an endoscope in accordance with the present invention is characterized in that a water proofing packing is mounted around the endoscope at its connecting portion or eyepiece portion and a protective cover is provided over the packing for preventing the packing from being damaged. The protective cover is secured to the endoscope to protect the packing while a water proof cover is removed from the endoscope. Further, in a preferred embodiment, a water proof cover to be covered on the endoscope at its connecting portion or eyepiece portion in water proof engagement with said packing is provided with a protective sleeve to protect the engaging face thereof when the water proof cover is removed from the endoscope. The protective sleeve is slidable between a protecting position to cover the engaging face and a retracted position to expose the face.

With the protective cover, the packing is protected from being damaged when the water proof cover is removed from the endoscope. Therefore, the high water proofing performance of the packing is maintained. Further with the protective sleeve, the smooth engaging face of the cover to be engaged with the packing is protected from being damaged when the water proof cover is removed from the endoscope.

DESCRIPTION OF THE PREFERRED EMBODIMENTS

Figure 1:
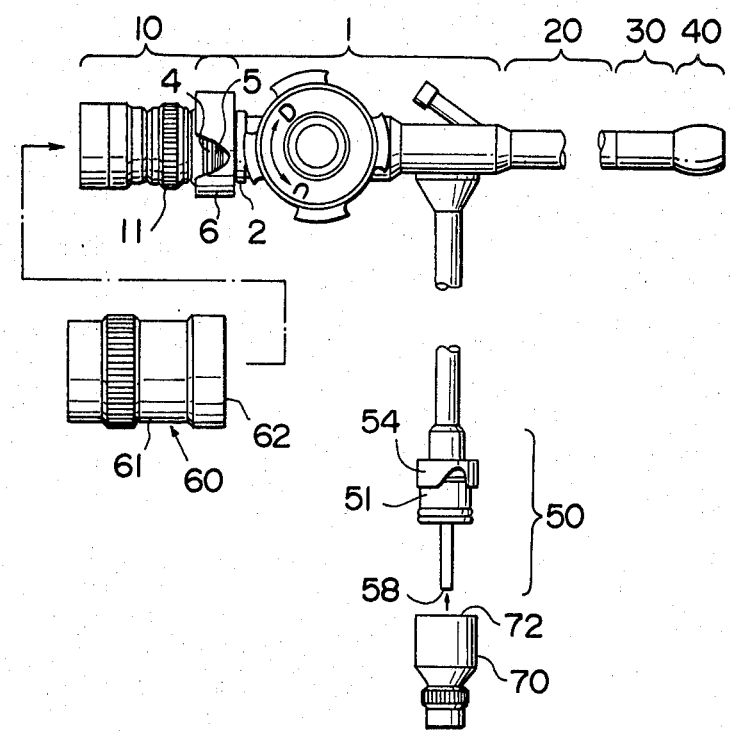
FIG. 1 is a partly cut away entire view of an endoscope employing water proof covers in accordance with the present invention.

Now the present invention will be described in detail with reference to particular embodiments thereof shown in the drawings.

Referring to FIG. 1, an endoscope is composed of an operating portion 1, an eyepiece portion 10 connected to a connecting portion 2 of the operating portion 1 where the water proofing structure for the present invention is provided, a flexible tube portion 20 connected with the operating portion 1 for passing therethrough remote control wires and optical fiber bundles, an angle portion 30 connected with the flexible tube portion 20, a hard tip portion 40 having a round face and functioning as an inspection head, a connector portion 50 provided with a connector 51 having a special water proofing structure for the present invention, and water proof covers 60 and 70 mounted on the eyepiece portion 10 and the connector portion 50, respectively, for water proofing those portions.

The eyepiece portion 10 is a non-water proofed portion provided with a diopter ring 11 and an eyepiece lens system. The connector portion 50 is also a non-water proofed portion provided with an exposed end face 58 of a light guiding optical fiber bundle to be located adjacent to a light source when it is connected with a socket of a light source system. The connector portion 50 is further provided with an electric terminal 59 (see FIG. 3) which is to be connected with an electric terminal in the light source system for connecting the light source with an operating button (not shown) provided on the operating portion 1. Thus, the eyepiece portion 10 and the connector portion 50 do not have a water proof structure, and accordingly, are desired to be water proofed.

The water proof cover in accordance with the present invention may be a cover for the eyepiece portion or a cover for the connector portion. Now an embodiment of the present invention will be described with reference to FIG. 2 in which the present invention is embodied into a water proof cover for an eyepiece portion.

Figure 2:
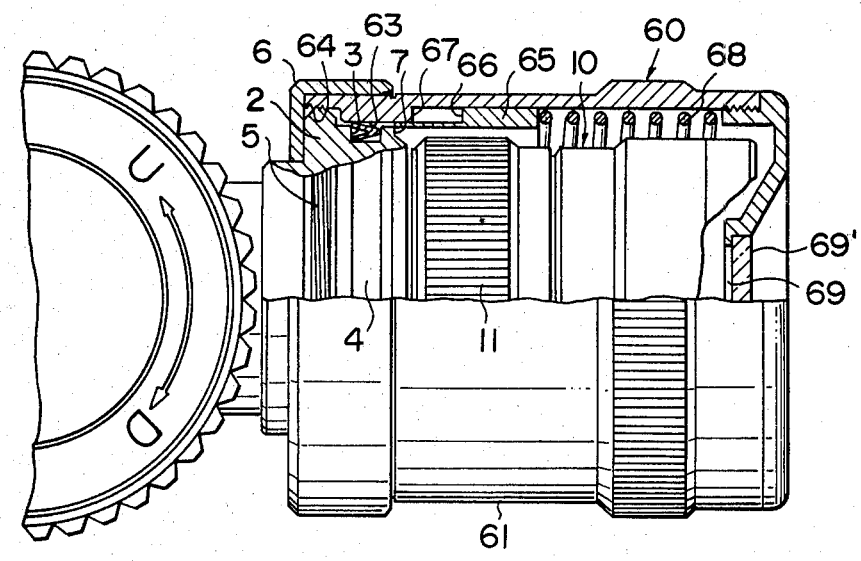
FIG. 2 is an enlarged longitudinal half sectional view showing an embodiment of the water proof cover adapted to the eyepiece of an endoscope.

Referring to FIG. 2 in which a water proof cover 60 is covered on the connecting portion 2 of the operating portion 1 to water proof the eyepiece portion 10, a water proofing packing ring 4 is mounted around the connecting portion 2 or neck within a packing groove 3 formed on the periphery of the connecting portion 2. Around the periphery of the connecting portion 2, there are further formed a male screw 5 on the large diameter portion on the operating portion side and a stepped stopper 7 on the eyepiece side. Further, a protective cover 6 which covers over the male screw 5 and the packing ring 4 is secured to the connecting portion 2 forming a space between the cover 6 and the screw 5 and the packing ring 4. The protective cover 6 has an open annular end on the eyepiece side to receive therein a water proof cover 60.

The water proof cover 60 has a cylindrical body portion 61 having an open end 62 (see FIG. 1) and a bottom with a window 69 closed with a glass 69'. On the internal face of the cylindrical body 61 near the open end 62 thereof are formed a female screw 64 to be screw engaged with said male screw 5 and an engaging face 63 to be engaged with said packing ring 4. Further, on the internal face of the water proof cover 60 is provided an axially slidable sleeve 65 for protecting the engaging face 63 when the water proof cover 60 is removed from the eyepiece portion 10. The protective sleeve 65 is made of hard rubber or the like and axially slidable to cover the engaging face 63 in response to removal of the cover 60 from the eyepiece portion 10. The slidable sleeve 65 is spring urged in the axial direction toward the engaging face 63 by means of a coil spring 68 inserted between the rear end of the sleeve 65 and the rear internal end or bottom of the cover 60 so that the sleeve 63 is slid to the position to cover and protect the engaging face of the water proof cover 60. The sleeve 65 has an abutment face 66 to be brought into abutment with an abutment face of the cover 60 at the rear end of the engaging face 63 so that the sleeve 65 is stopped at the position to cover the engaging face 63.

In the above mentioned embodiment of the present invention, the water proof cover 60 is covered on the eyepiece portion 10 with the female screw 64 thereof engaged with the male screw 5 of the connecting portion 2 of the endoscope and the open end 62 thereof is screw engaged with the connecting portion 2. Further, the smooth engaging face 63 of the cover 60 is engaged with the packing ring 3 in a water proof or liquid tight fashion. Thus, the water proof cover 60 is liquid tightly mounted on the eyepiece 10. As the cover 60 is mounted on the eyepiece 10, the front end of the slidable sleeve 65 abuts against the stepped stopper 7 and is retracted from the covering position to the retracted position to expose the smooth engaging face 63. The exposed engaging face 63 is liquid tightly engaged with the packing ring 3. Thus, the eyepiece portion 10 is perfectly water proofed.

Figure 3:
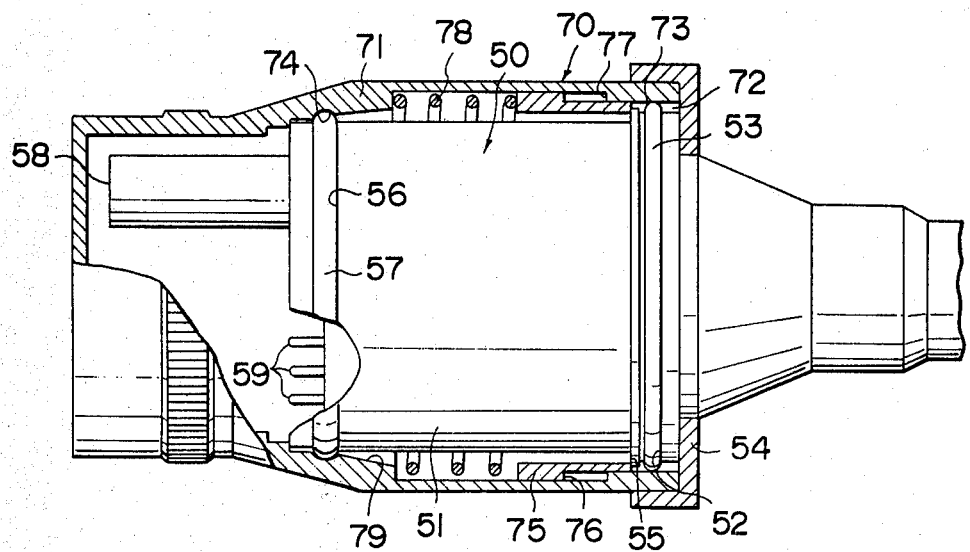
FIG. 3 is an enlarged longitudinal sectional view showing an embodiment of the water proof cover adapted to the connector of an endoscope.

Another embodiment of the present invention adapted to the connector portion 50 will hereinbelow be described in detail with reference to FIG. 3. Referring to FIG. 3, a water proof cover 70 is covered on the connector portion 50. The connector portion 50 is provided at its neck portion connected with the flexible tube portion (not shown) with a protective cover 54 similar to said protective cover 6 in the first embodiment shown in FIG. 2. The protective cover 54 is secured to the neck portion of the body 51 of the connector portion 50 to cover a part of the body portion of the neck side where the body is provided on its periphery with a packing ring 53 fixed in a packing groove 52. The body portion 51 of the connector portion 50 is further provided on its rear periphery with a click spring ring 57 fixed in an annular groove 56. Further, the body 51 is provided in the vicinity of said water proof packing ring 53 with a stopper portion 55 faced rearwards which functions as said stepped stopper 7 in the first embodiment shown in FIG. 2.

On the other hand, the water proof cover 70 is provided on the internal periphery thereof on the open end 72 side with a smooth engaging face 73 to be engaged with said packing ring 53 for water proof. Further, in the vicinity of the engaging face 73 on the rear side there is provided a slidable sleeve 75 similar to said slidable sleeve 65. The slidable sleeve 75 is slidable between a covering position to cover and protect the engaging face 73 and a retracted position to expose the engaging face 73. There is provided a coil spring 78 between the rear end of the slidable sleeve 75 and a stepped portion of the cover 70 to spring urge the sleeve 75 into the protecting position to cover the engaging face 73. The sleeve 75 has an abutment face or stepped portion 76 to abut against a stopper 77 formed at the rear end of the engaging face 73 so that the sleeve 75 is stopped at the protecting position. The water proof cover 70 is provided on the internal face thereof further with a click groove 74 to receive said click spring ring 57 when the cover 70 is covered on the connector portion 50. Between said stepped portion to interpose said coil spring 78 in cooperation with said slidable sleeve 75 and the click groove 74 is formed a tapered portion 79 to guide the click spring ring 57 into the click groove 74.

When the water proof cover 70 is covered on the connector portion 50, the cover 70 is inserted into the position where the open end 72 thereof enters between the protective cover 54 and the packing ring 53 and the click spring ring 57 is click engaged with the click groove 74. As the cover 70 is moved into such a position, the front end of the slidable sleeve 75 abuts against the stopper portion 55 and moved back to the retracted position to expose the engaging face 73 and the engaging face 73 engages with the packing ring 53. Since the engaging face 73 is protected by the slidable sleeve 75 and the packing ring 53 is protected by the protective cover 54 while the cover 70 is removed from the connector portion 50, the face 73 and the ring 53 are well protected from being damaged and accordingly maintain good condition for water proof. Thus, high water proof performance is enjoyed in accordance with this embodiment.

Still another embodiment will now be described in detail with reference to FIG. 4. The embodiment shown in FIG. 4 pertains to an eyepiece water proofing cover 80 which enables operation of the diopter ring 11 with the cover 80 mounted thereon. In other words, with the water proof cover 80 in accordance with this embodiment the diopter ring 11 can be manually operated with the cover 80 mounted on the eyepiece portion. In actual operation of an endoscope, it is often desirable that the operator handles the endoscope with a dirty hand and the diopter ring should be rotated for diopter adjustment particularly when the observer changes. This embodiment is very useful for such use.

Figure 4:
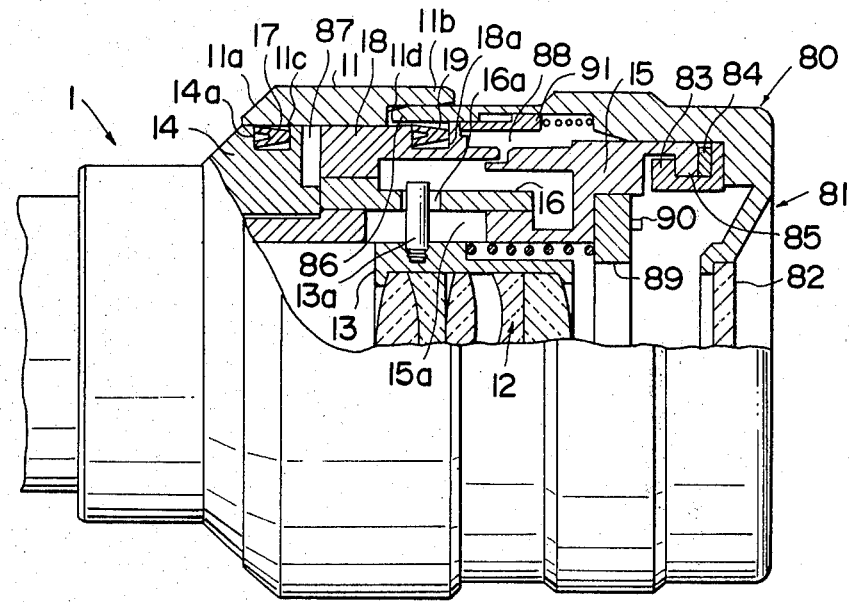
FIG. 4 is an enlarged longitudinal half sectional view showing another embodiment of the water proof cover adapted to the eyepiece of an endoscope which enables operation of a diopter ring with the water proof cover mounted thereon.

Referring to FIG. 4, a lens system 12 is supported by a lens holder 13 and movable in the direction of the optical axis thereof for adjusting diopter. The lens holder 13 has a pin 13a fixed thereto and engaged with a cam 16a formed in a cam cylinder 16 rotatably provided on a fixed cylinder 15. The fixed cylinder 15 is secured to an eyepiece mounting portion 14 of the operating body portion 1 and is provided with a key slot 15a through which said pin 13a extends. With this arrangement, the lens holder 13 axially moves as the cam cylinder 16 rotates. On the outer periphery of the eyepiece mounting portion 14 is provided an annular packing groove 14a in which a packing ring 17 having a Y-shaped cross section is mounted. Further, there is provided another packing groove 18a on the periphery of a cylindrical intermediate ring 18 which is secured to and connected between the diopter ring 11 and the cam cylinder 16. In the second packing groove 18a is mounted a second packing ring 19 having a Y-shaped cross section. The diopter ring 11 has an extended portion 11a to cover said packing groove 14a and the packing ring 17 on the endoscope body portion side. The extended portion 11a has a flat inner face 11c to be engaged with and slidable on the packing ring 17. The diopter ring 11 further has a rearwardly extending portion 11b extending over the second packing ring 19 forming a space 11d between itself and the packing ring 19. The water proof cover 80 has a bottom 81 provided with a window having a glass 82 liquid tightly fixed thereto. The glass 82 may of course be made of a plastic material like acrylic resin. The water proof cover 80 has at its bottom bayonet claws 83 and leaf springs 84 and is mounted to the eyepiece portion with the engagement with the bayonet ring 85 formed on the fixed cylinder 15. The open front end 86 of the water proof cover 80 is inserted tightly into the space 11d between the rearwardly extending covering portion 11b and the packing ring 19 with such tightness that the diopter ring 11 together with the intermediate ring 18 may be rotated in slidable engagement with the water proof cover 80.

In the state where the water proof cover 80 is fixed to the eyepiece portion at the fixed cylinder 15 with the bayonet mount 83,84,85 as shown in FIG. 4, the diopter ring 11 is rotatable with respect to the eyepiece portion and the water proof cover 80. By rotating the diopter ring 11, the intermediate ring 18 and the cam cylinder 16 are rotated and the diopter is adjusted. Thus, it is possible to rotate the diopter ring 11 with respect to the eyepiece mounting portion 14 and the water proof cover 80. Therefore, it is possible to adjust diopter with the water proof cover mounted on the eyepiece portion. Since the packing rings 17 and 19 function to water proof on both sides of the diopter ring 11, there is no fear of water leakage at the spaces 87 and 88 between the eyepiece mounting portion 14 and the intermediate cylinder 18, and the fixed cylinder 15 and the intermediate cylinder 18. Further, of course, the insulating ring 89 and the synchronizing contact 90 provided thereon located at the rear end of the eyepiece portion are water proofed by the water proof cover 80.

In the above described embodiment, the extended portion 11a and the cover portion 11b of the diopter ring 11 are integrally formed with the diopter ring 11. It may be noted, however, that these portions may be integrally formed with the intermediate cylinder 18.

Further, it is possible to make the water proof cover of a transparent material like acrylic resin as a whole.

Furthermore, it is possible to provide a slidable sleeve 91 like said slidable sleeves 65 and 75 for protecting the engaging face of the water proof cover 80 at the internal near the open end 86 thereof. In other words, the slidable sleeve 91 is an option and may not be provided on the water proof cover. This is so also in the above described embodiments shown in FIGS. 2 and 3.

I claim:

1. Structure for waterproofing a portion of an endoscope, said endoscope including an operating portion and a portion to be waterproofed, comprising:
   an annular connecting means for forming a connecting neck on an endoscope between an operating portion thereof and a portion to be waterproofed, said annular connecting means having a packing ring mounted therearound;
   a protective cover fixed to said connecting means for covering and protecting said packing ring, said protective cover forming a space surrounding said packing ring;
   a waterproof cover having a bottom and an open end opposite to said bottom, said open end being adapted for insertion into said space, said waterproof cover having a smooth engaging face on an interior portion thereof for liquid tightly engaging with said packing ring; and
   means for firmly mounting said waterproof cover on said connecting means at a position where said smooth engaging face is liquid-tightly engaged with said packing ring.

2. The structure of claim 1 wherein said waterproof cover has a transparent viewing portion at its bottom.

3. The structure of claim 1 wherein said waterproof cover has a protecting means for protecting said smooth engaging face while the waterproof cover is removed from said space.

4. The structure of claim 3 wherein said protecting means is a slidable sleeve movable between a protecting position to cover and protect said engaging face and a retracted position to expose said engaging face, said slidable sleeve being spring urged toward the protecting position and moved to said retracted position in response to the mounting of said waterproof cover in said space.

5. The structure of claim 4 wherein said connecting means includes stopper means and said slidable sleeve has an abutment portion for engaging the stopper means for retraction of the slidable sleeve as the waterproof cover is inserted into the space surrounding the packing ring.

6. The structure of claim 1 wherein said structure comprises a second packing ring and said annular connecting means includes a diopter ring assembly, said diopter ring assembly being operative for adjustment of said eyepiece portion and wherein said protective cover is fixed to said diopter ring, said second ring is mounted on said connecting means, and said diopter ring is in slidable and liquid-tight contact with said second packing ring.

7. Structure for waterproofing a portion of an endoscope, said endoscope including an operating portion and a portion to be waterproofed, comprising:
   an annular connecting means for forming a connecting neck on an endoscope between an operating portion thereof and a portion to be waterproofed, said annular connecting means having a packing ring mounted therearound;

a protective cover fixed to said connecting means for covering and protecting said packing ring, said protective cover forming a space surrounding said packing ring;

a waterproof cover having a bottom and an open end opposite to said bottom, said open end being adapted for insertion into said space, said waterproof cover having a smooth engaging face on an interior portion thereof for liquid tightly engaging with said packing ring; and means for firmly mounting said waterproof cover on said connecting means at a position where said smooth engaging face is liquid-tightly engaged with said packing ring, said waterproof cover having a protecting means for protecting said smooth engaging face while the waterproof cover is removed.

8. The structure of claim 7 wherein said protecting means is a slidable sleeve movable between a protecting position to cover and protect said engaging face and a retracted position to expose said engaging face, said slidable sleeve being spring urged toward the protecting position and moved to said retracted position in response to mounting thereof in said space.

9. The structure of claim 8 wherein said connecting means includes stopper means and said slidable sleeve has an abutment portion for engaging the stopper means for retraction of the slidable sleeve as the waterproof cover is inserted into the space surrounding the packing ring.

* * * * *